(12) United States Patent
Dennis

(10) Patent No.: US 10,772,831 B2
(45) Date of Patent: Sep. 15, 2020

(54) PHARMACEUTICAL CAPSULES FOR MEDICATION ADHERENCE MONITORING AND METHODS OF FORMING THE SAME

(71) Applicant: University of Florida Research Foundation, Inc., Gainesville, FL (US)

(72) Inventor: Donn Dennis, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 213 days.

(21) Appl. No.: 15/627,699

(22) Filed: Jun. 20, 2017

(65) Prior Publication Data

US 2017/0367976 A1 Dec. 28, 2017

Related U.S. Application Data

(60) Provisional application No. 62/353,108, filed on Jun. 22, 2016.

(51) Int. Cl.
| | |
|---|---|
| *A61K 9/00* | (2006.01) |
| *A61K 49/00* | (2006.01) |
| *A61B 5/00* | (2006.01) |
| *A61B 5/08* | (2006.01) |
| *A61K 9/48* | (2006.01) |
| *G01N 33/497* | (2006.01) |
| *A61B 5/07* | (2006.01) |

(52) U.S. Cl.
CPC ............ *A61K 9/0056* (2013.01); *A61B 5/082* (2013.01); *A61B 5/4833* (2013.01); *A61K 9/4833* (2013.01); *A61K 49/0004* (2013.01); *G01N 33/497* (2013.01); *A61B 5/073* (2013.01); *A61K 49/00* (2013.01)

(58) Field of Classification Search
None
See application file for complete search history.

(56) References Cited

U.S. PATENT DOCUMENTS

| | | | |
|---|---|---|---|
| 5,032,074 A | 7/1991 | Muto et al. | |
| 5,930,984 A * | 8/1999 | Furuya | A61J 3/072 53/471 |
| 6,350,468 B1 * | 2/2002 | Sanso | A61K 9/4808 424/456 |
| 7,820,108 B2 | 10/2010 | Lampotang | |
| 9,047,746 B1 | 6/2015 | Euliano et al. | |
| 2009/0162430 A1 | 6/2009 | Mohmoud et al. | |
| 2010/0255598 A1 | 10/2010 | Melker et al. | |
| 2012/0116359 A1 * | 5/2012 | Hafezi | A61J 3/06 604/891.1 |
| 2014/0294675 A1 | 10/2014 | Melker et al. | |
| 2014/0302133 A1 | 10/2014 | Van Rooyen et al. | |
| 2014/0341983 A1 | 11/2014 | Dennis et al. | |

OTHER PUBLICATIONS

Lars Osterberg, M.D. and Terrence Blaschke, M.D., Drug Therapy: Adherence to Medication, The New England Journal of Medicine in 2005.
Foreign search report for PCT/US17/38261 dated Jul. 5, 2017.

* cited by examiner

*Primary Examiner* — Xiaoyun R Xu

(57) ABSTRACT

Provided according to embodiments of the invention pharmaceutical capsules that include a capsule body and a capsule cap, wherein the capsule cap envelops an open end of the capsule body to form a capsule core; and an adherence sheath that envelops a portion of the capsule core. Related capsules and methods of making such capsules are also provided herein.

30 Claims, 5 Drawing Sheets

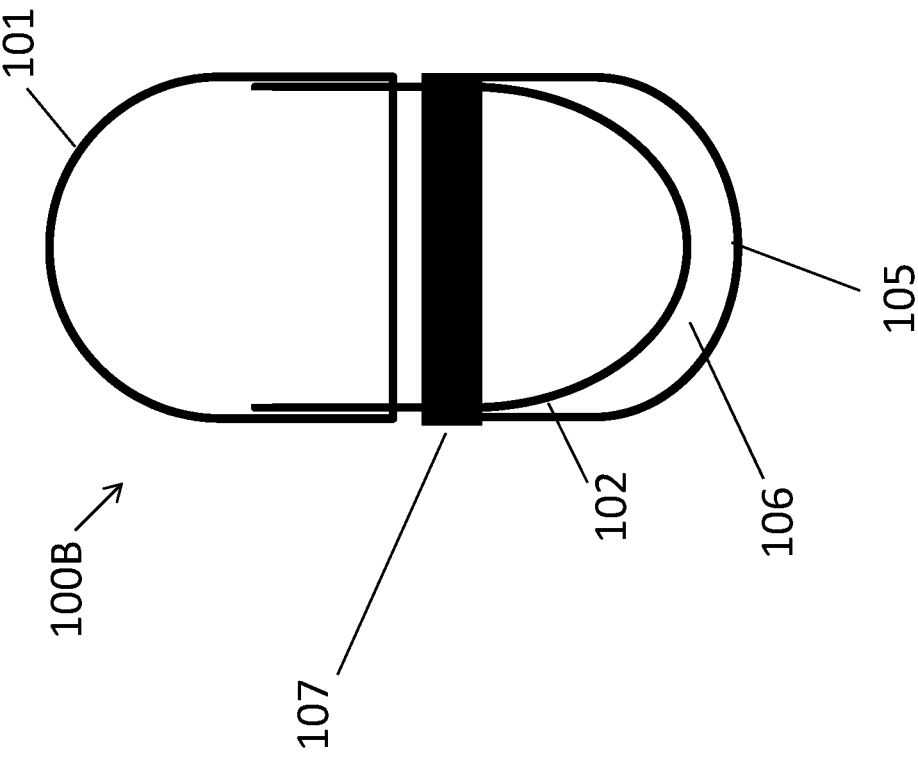
FIGURE 1B: Adherence Capsule
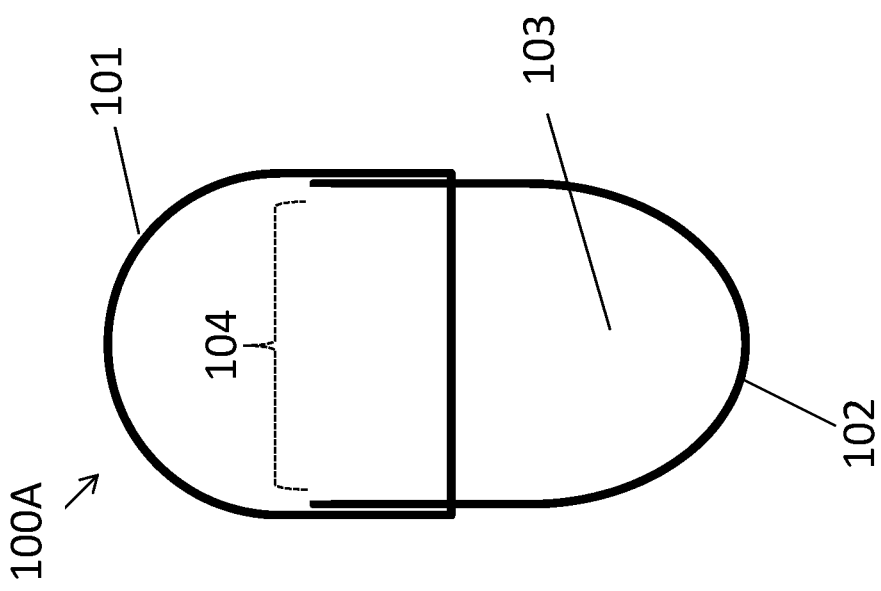
FIGURE 1A: Standard Capsule

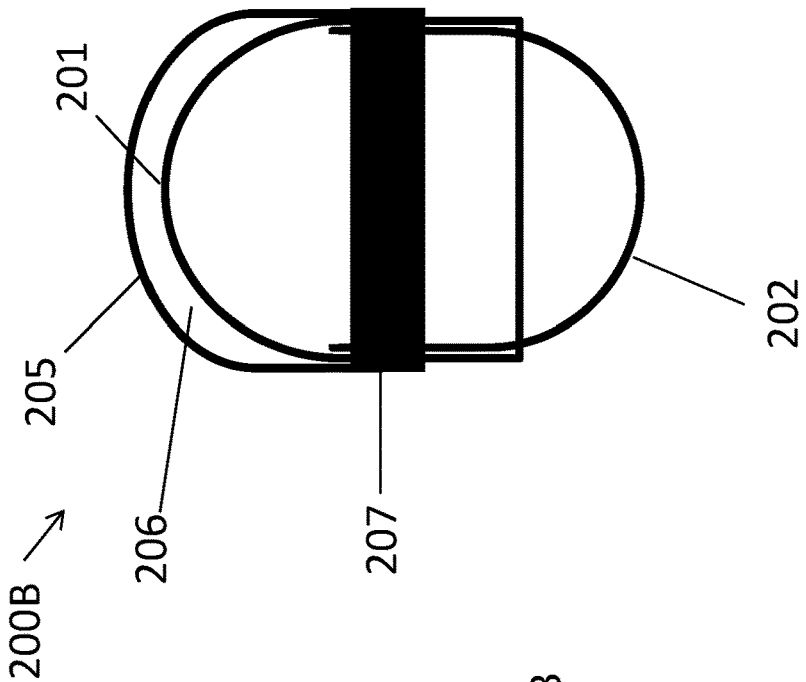
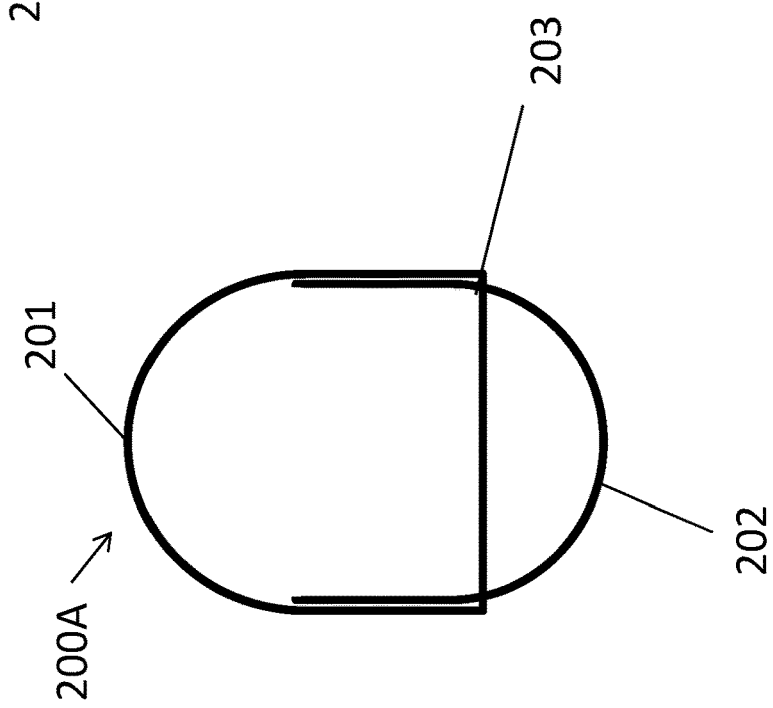

US 10,772,831 B2

PHARMACEUTICAL CAPSULES FOR MEDICATION ADHERENCE MONITORING AND METHODS OF FORMING THE SAME

CROSS-REFERENCE TO RELATED APPLICATIONS

This application claims the benefit of U.S. Provisional Application No. 62/353,108, filed Jun. 22, 2016, the contents of which are incorporated herein by reference in their entirety.

FIELD OF THE INVENTION

The present invention relates to pharmaceutical capsules and methods for encapsulating pharmaceutical compositions. The present invention also relates to medication adherence monitoring products and methods.

BACKGROUND OF THE INVENTION

Non-compliance of patients to drug regimens prescribed by their physicians results in excessive healthcare costs estimated to be around $100 billion per year through lost work days, increased cost of medical care, higher complication rates, as well as drug wastage. In addition, non-compliance of drug regimens by patients during clinical trials may result in denial of FDA clearance for otherwise viable drugs. It is estimated that the average non-adherence rates among patients in clinical trials receiving treatment for chronic conditions can be as high as 57%. See, *The New England Journal of Medicine in* 2005 (Lars Osterberg, M.D. and Terrence Blaschke, M.D., "*Drug Therapy: Adherence to Medication*"). If a drug fails to achieve approval in part because participants are not taking the study medication, significant money is wasted and drugs that may be useful to patients never gain approval. Non-compliance refers to the failure to take the prescribed dosage at the prescribed time which results in under-medication or over-medication.

Devices, systems and methods for breath-based monitoring medication adherence are known in the art. Examples of such devices, systems and methods can be found, for example, in U.S. Pat. No. 7,820,108, and U.S. Publication Nos. 2014/0294675, 2010/0255598 and 2014/0341983, the contents of which are incorporated herein by reference in their entirety. Despite the success of such methods, there remains a need in the art for improved products, devices, systems and methods for medication adherence monitoring.

SUMMARY OF THE INVENTION

Provided according to embodiments of the invention are pharmaceutical capsules for medication adherence monitoring. Such pharmaceutical capsules include a capsule body and a capsule cap, wherein the capsule cap envelops an open end of the capsule body to form a capsule core; and an adherence sheath that envelops a portion of the capsule core. The adherence sheath may be sealed to the capsule core in a number of ways including via chemical or mechanical means, including the use of a circumferential band.

Also provided are pharmaceutical capsules according to embodiments of the invention that further include a medication adherence marker (MAM) contained in a space between the adherence sheath and the capsule core. In some cases, the MAM is a solid, semi-solid or liquid at standard temperature and pressure. In particular embodiments, the MAM includes a secondary or tertiary alcohol, and in other particular embodiments, the MAM maybe include an electronic device.

Further provided according to embodiments of the invention are methods of forming pharmaceutical capsules that include enveloping an open end of a capsule body with a capsule cap to form a capsule core; and enveloping a portion of the capsule core with an adherence sheath. The adherence sheath may further be sealed to the capsule core by any suitable method.

BRIEF DESCRIPTION OF THE DRAWINGS

FIG. 1A illustrates the structure of a standard pharmaceutical capsule. FIG. 1B illustrates a pharmaceutical capsule according to an embodiment of the present invention.

FIG. 2A illustrates the structure of a standard over-encapsulating capsule. FIG. 2B illustrates an over-encapsulating capsule according to an embodiment of the present invention.

DETAILED DESCRIPTION OF EMBODIMENTS OF THE INVENTION

Figure 3:
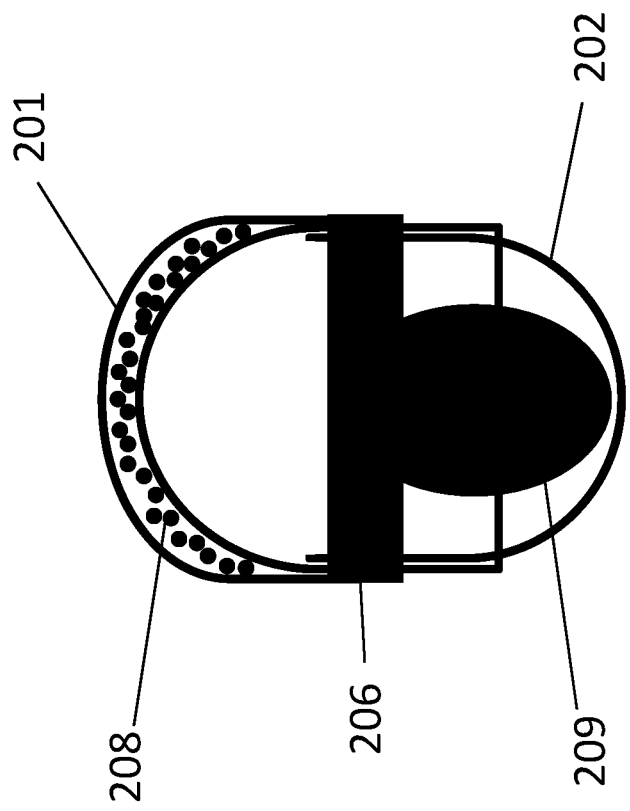
FIG. 3 illustrates an over-encapsulating capsule according to an embodiment of the present invention that includes a solid tablet including an active pharmaceutical ingredient (API) and a medication adherence marker (MAM).

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It will be understood that when an element is referred to as being "on" or "adjacent" to another element, it can be directly on or directly adjacent to the other element or intervening elements may also be present. In contrast, when an element is referred to as being "directly on" or "directly adjacent" to another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers refer to like elements throughout the specification.

It will be understood that, although the terms first, second, etc. may be used herein to describe various elements, these elements should not be limited by these terms. These terms are only used to distinguish one element from another. Thus, a first element discussed below could be termed a second element without departing from the teachings of the present invention.

Embodiments of the present invention are described herein with reference to schematic illustrations of idealized embodiments of the present invention. As such, variations from the shapes of the illustrations as a result, for example, of manufacturing techniques and/or tolerances, are to be expected.

Provided according to embodiments of the invention are pharmaceutical capsules for medication adherence monitoring, also referred to herein as "adherence capsules," or AdhCaps. In some embodiments, the capsules include a capsule body and a capsule cap, wherein the capsule cap envelops an open end of the capsule body to form a capsule core; an adherence sheath that envelops a portion of the capsule core. The adherence sheath is applied to a pharmaceutical capsule to provide a payload space for a medication adherence marker (MAM), while also separating the MAM from any active pharmaceutical ingredient (API) or excipient therein.

A medication adherence marker (MAM), as used herein, refers to any solid, semi-solid, liquid or gas (at standard temperature and pressure), including chemicals (including isotopically-enriched compounds), biologics, metals or electronic devices, that is included in or with a pharmaceutical capsule to provide an indication of whether an individual has ingested the medication (or empty pharmaceutical capsule, e.g., in a double blind clinical trial). In some embodiments of the invention, the MAM is a chemical compound present in the capsule that after dissolution of at least part of the capsule in the individual's stomach will produce a detectable marker in the individual's breath. In some cases, the detectable marker is the MAM itself, but in other cases, it is a metabolite or other compound produced by the MAM. Examples of MAMs, devices used to detectable markers, and methods of detection can be described in U.S. Pat. No. 7,820,108, and U.S. Publication Nos. 2014/0294675, 2010/0255598 and 2014/0341983, which are herein incorporated by reference in their entirety. In particular embodiments, the MAM comprises a secondary or tertiary alcohol, such as 2-butanol, which is a considered a generally regarded as safe (GRAS) compound. In another embodiment, the MAM comprises a secondary or tertiary alcohol that is isotopically-enriched, e.g., with one or more deuterium atoms.

In some embodiments of the invention, the MAM may be an electronic sensing device, including a sensor, chip, RF device, or the like. The electronic MAM present in the capsule may interact with a device including a processor or detector (such as, e.g., a badge worn by the individual). In some cases, the electronic sensing device may communicate with the processing device to provide an indication that the device has been ingested as part of the pharmaceutical capsule. For example, the electronic sensing device may note a change in environment when the capsule is dissolved (e.g., more acidic) and may provide an indication to the processing device, which may process the information or forward the information to other processing devices or displays.

The basic structure of a standard pharmaceutical capsule is shown in FIG. 1A. Here, the pharmaceutical capsule 100A includes a capsule cap 101 and capsule body 102, whereby the capsule cap 101 envelops the open end 104 of the capsule body 102 to form the capsule core 103. The capsule body 102 and/or the capsule cap 101 may be secured together by any suitable method. In some cases, the capsule body 102 and/or the capsule cap 101 have ridges or other complementary surface features that may allow the two pieces to bind or "lock" the pieces together and secure the capsule core 103. Other methods, which may be useful for liquid APIs include Liquid Encapsulation by Microspray (LEMS) processes, in which chemical reaction or physical dissolution/solidification (collectively referred to herein as "chemical processes") of a portion of the capsule cap 101 and/or capsule body 102 is used to seal the two pieces together; likewise circumferential banding (e.g., a band of molten gelatin or hydroxypropyl methylcellulose (HPMC) can be wrapped around the joint of the capsule cap 101 and capsule body 102) to form a tight seal for APIs, when needed (e.g, liquids, semi-solids).

Any suitable capsule material may be used, including an animal-based material such as gelatin (e.g., a hard shell gelatin material), vegetarian or vegan-based materials (e.g., HPMC). Commercially available capsules may also be used. For example, standard animal-based commercial capsules that may be used include those that are used to encapsulate solids, such as, e.g., Coni-Snap® (Capsugel, Inc.), Quali-G™ and Prism-G™ (Qualicaps, LLC) and those that are used to encapsulate liquids, such as, e.g., LiCaps® (Capsugel, Inc). Standard vegetarian commercial capsules include Vcaps® (Capsugel, Inc.) and other hypromellose-based capsules. Non-standard capsules may also be used. For example, over-encapsulation capsules meant for clinical trials/double blind studies may also be used, such as, e.g., DBcaps® (Capsugel, Inc.).

An adherence capsule according to an embodiment of the present invention is shown in FIG. 1B. As with the standard capsules, the adherence capsules include a capsule cap 101 that envelops the open end 104 of the capsule body 102 to form a capsule core 103. In addition, however, the adherence capsule 100B includes an adherence sheath 105 that envelops a portion of the capsule core 103. In FIG. 1B, the adherence sheath 105 envelops the capsule body 102 portion of the capsule core 103, but the adherence sheath 105 may also envelop the capsule cap 101 portion of the capsule core 103, as will be discussed in further detail below. The adherence sheath 105 provides a payload space 106 between the capsule core 103 and the adherence sheath 105 whereby a medication adherence marker (MAM) may be placed. A portion of the adherence sheath 105 may be sealed to the capsule core 103 to secure the adherence marker within the payload space 106 between the capsule core 103 and the adherence sheath 105.

The adherence sheath 105 may be sealed to the capsule core 103 by any suitable method or device. For example, in FIG. 1B, the adherence sheath 105 is sealed to the capsule core 103 with a circumferential band 107. The circumferential band 107 may be made of the same types of materials as the pharmaceutical capsules themselves, including compatible animal (e.g., hard shell gelatin material), vegetarian or vegan based materials (e.g., HPMC). In some cases, hard gel or HPMC banding techniques, which are known in the art, may be used to form the circumferential band 107. The circumferential band 107 may be placed around any portion on the adherence sheath 105 but in some embodiments, such as that shown in FIG. 1B, the circumferential band 107 is secured on the adherence sheath 105 at the capsule body 102 portion, not touching the capsule cap 101, so that any MAM in the payload space 106 will not enter the capsule core 103.

Other methods of securing/sealing, air venting, and properly positioning the adherence sheath 105 to the capsule core 103 may be used as well. For example, the inside of the adherence sheath 105 and/or the outside of the capsule core 103 may be ridged or the adherence sheath 105 and the capsule body 102 may include complementary features that bind or "lock" the pieces together and position the adherence sheath 105 to the capsule core 103 prior to definitive sealing by banding or LEMS. Recall that LEMS or other chemical process may be used to seal the adherence sheath 105 to the capsule core 103.

While in FIG. 1B, the adherence sheath 105 is shown as enveloping the capsule body 102 portion of the capsule core 103, in some cases, it may be preferable for the adherence sheath 105 to envelope a capsule cap 101 portion of the capsule core 103. For example, this may be useful for over-encapsulating capsules (e.g., DBcaps®). FIG. 2A provides an illustration of the general structure of an over-encapsulating capsule 200A, whereby the capsule cap 201 envelops the open end of the capsule body 202 to form the capsule core 203. The size and shape of such over-encapsulating capsules 200A allows for encapsulation of commercial pharmaceutical forms, including tablets or other capsules. Over-encapsulating capsules 200A are frequently used in double blind studies so that the patient cannot see the size, shape, or color of the tablet (or other pharmaceutical form) and so is not biased by the form of the medication. The capsule materials and methods of securing the capsule cap 201 and the capsule core 202 together include those described with respect to the standard capsules.

FIG. 2B provides an illustration of an adherence capsule according to an embodiment of the invention whereby an over-encapsulating capsule 200B is used. In this case, the adherence sheath 205 envelops the capsule cap 201 portion of the capsule core 203, which provides a payload space 206 between the capsule cap 201 and the adherence sheath 205. In the embodiment shown in FIG. 2B, a circumferential band 207 is used to secure the adherence sheath 205 to the capsule cap 201 portion of the capsule core 203, and the methods of securing and sealing (e.g., banding, LEMS) described above with respect to standard capsules are also applicable with the over-encapsulating capsules.

Whether the adherence sheath envelops the capsule cap portion or the capsule body portion of the capsule core depends on a number of factors, including the diameter of the capsule cap, capsule core, and the adherence sheath. In some cases, in order to avoid the need to manufacture custom adherence sheaths for the pharmaceutical capsules according to embodiments of the invention, a second capsule cap or capsule body may be used as the adherence sheath. Referring to FIG. 1B, in some embodiments, the adherence sheath 105 is second capsule body 103, or a second capsule body 103 that has been modified, such as, e.g., shortened. For example, in some cases, a portion of the open end of a capsule body is cut off to form the adherence sheath 105. This may allow for the adherence sheath 105 to be sufficiently long to secure to the sides of the capsule body 103 but short enough so that the adherence sheath 105 does not touch the capsule cap 101. If the adherence sheath 105 and the capsule cap 101 are adjacent/touching, it may be possible for the MAM to enter the capsule core 103, and depending on the sensitivity of the MAM and the API/excipients, this may not be desirable. This may not always be problematic, however, depending on (a) the sensitivity of the MAM and API/excipients and/or (b) how the adherence sheath is secured to the capsule core, so in some embodiments, the adherence sheath 105 may be adjacent to the capsule cap 101. Referring to FIG. 2B, in some cases, a second capsule cap may be used as the adherence sheath 205. The second capsule cap may be also be modified, e.g., shortened, if desired.

Also provided for according to embodiments of the invention are the adherence capsules described herein that further include a MAM in the payload space, whether the payload space is between the adherence sheath and the capsule cap portion of the capsule core or between the adherence sheath and the capsule body portion of the capsule core. FIG. 3 shows the pharmaceutical capsule shown in FIG. 2B with a MAM 208 and an active pharmaceutical ingredient (API) 209, which, in this embodiment, is provided in tablet form (and may include pharmaceutically acceptable excipients), but may be in any suitable pharmaceutical form. As can be seen in FIG. 3, the MAM 208 and the API 209 are physically separated from each other and so the MAM 208 cannot affect the stability or properties of the API 209. Another benefit is that MAM 208 is only separated from the outside environment by one relatively thin layer of capsule material. The thickness of the capsule wall(s) significantly affects how fast the MAM enters the stomach, and thus, in some cases, how quickly the MAM-generated adherence marker can be detected by a sensor or other detection device. The speed of detection may be important for patient compliance with medication adherence monitoring systems and devices.

At present, commercially available hard gel pharmaceutical capsules typically have a thickness in a range of 0.08 to 0.13 mm (e.g., about 0.11 mm) and so in some embodiments described herein, only about 0.08 to 0.13 mm of the hard gelatin material needs to dissolve before the MAM is released into the individual's body. Furthermore, an even thinner adherence sheath may be produced, which may further decrease the time it takes for the MAM to be released into the body.

The adherence capsules described herein may provide a number of benefits for medication adherence monitoring. First, as described above, the MAM and the API are physically separated from each other and so the MAM cannot affect the stability or properties of the API. Additionally, the presence of the MAM in the capsule does not affect the volume or geometry of the capsule core and should have no appreciable effect on the pharmacokinetics of the API. Furthermore, to the patient/individual ingesting the medication, the adherence capsules will appear very similar to a standard capsule which may improve compliance with the drug regimen. Another benefit is that commercially available pharmaceutical capsules may be used (or modified slightly), which may decrease the need for expensive manufacturing of new types of capsules, and the sealing/banding processes for the adherence sheath are also already known and used in other types of capsules. In addition, any type of material can be used for capsules, and the adherence capsules be used with solid, semi-solid, liquid or gas MAMs, as well as any type of API.

Also provided according to embodiments of the invention are methods of forming the pharmaceutical capsules described herein. In some embodiments, the methods include enveloping an open end of a capsule body with a capsule cap to form a capsule core; and enveloping a portion of the capsule core (capsule cap or capsule body) with an adherence sheath. In some cases, the methods further include sealing the adherence sheath to the portion of the capsule core. As described above, in some embodiments, the seal is formed by securing a band circumferentially around a portion of the adherence sheath that envelops the portion of the capsule core. However, in other embodiments, the seal is formed by chemically bonding or dissolving/adhering a portion of the adherence sheath to the capsule core. Further embodiments include placing a medication adherence marker (MAM) in the adherence sheath before enveloping the portion of the capsule core with the adherence sheath. Placing a pharmaceutical tablet or capsule with the API (and optionally pharmaceutically acceptable excipients) within the capsule core may also be performed.

Example 1

The detection time of a MAM (2-butanol) in the breath of individuals using different types of pharmaceutical capsule configurations was investigated in various prospective randomized Good Clinical Practice (GCP) trials. All of the capsules used 2-butanol as the MAM but the different capsule configurations resulted in varying capsule wall thicknesses. Across the studies, subjects were fed ad lib and had a wide demographic profile with no enrollment exclusions.

Figure 4:
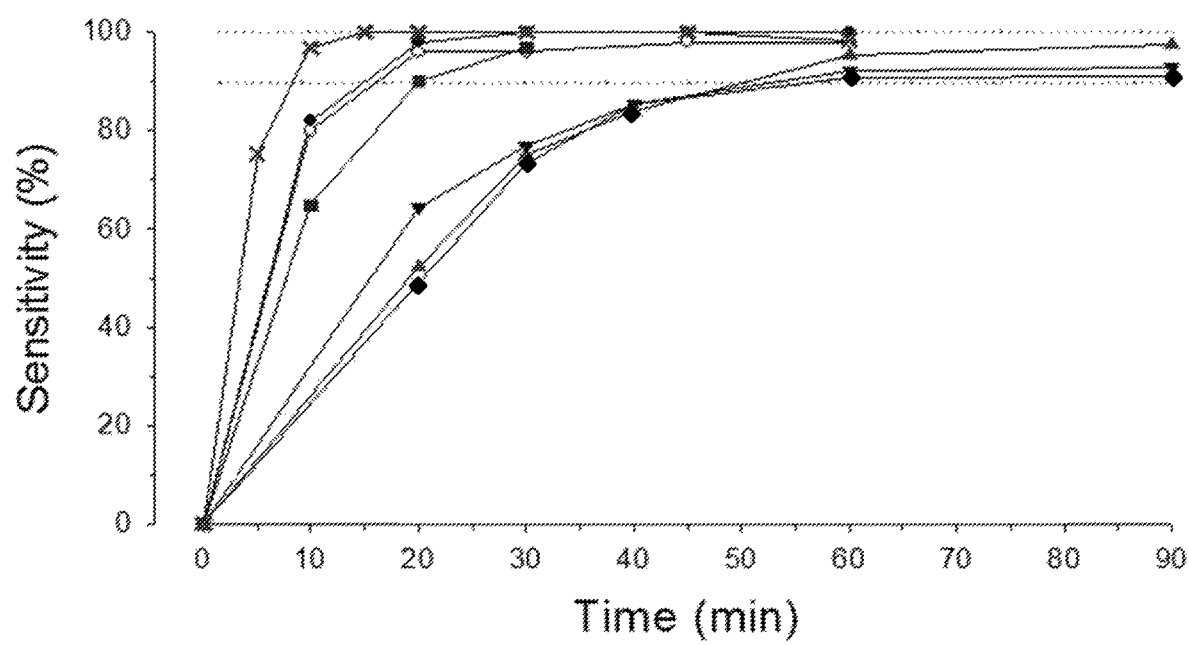
FIG. 4 shows a graph plotting the detection (sensitivity) of 2-butanol ingestion (as measured by a rise in 2-butanone breath levels ≥5 parts per billion [ppb] above baseline values) in humans over time for various capsule configurations having different total gelatin wall thicknesses. This total gelatin barrier (thickness) breaks down in the stomach in order to release the 2-butanol into the gastric environment; 2-butanol is then converted by the body to the ketone, 2-butanone, which is predominantly excreted in the breath. The diamond (♦) and triangle (▲) data points were obtained from 40 mg of 2-butanol inside a softgel capsule placed inside a hardgel capsule (total gelatin thickness of 0.87 mm). The inverted triangle (▼) data points were obtained from 50 mg of 2-butanol inside a thin softgel capsule placed inside a hardgel capsule (total gelatin thickness of 0.62 mm). The square (■) data points were obtained from 40 mg 2-butanol in a hard gel capsule placed in another hard gel capsule (total gel thickness of 0.22 mm). The black circle (●) and white circle (○) data points were obtained from 40 mg of 2-butanol in a hardgel capsule placed inside other hardgel capsule (total gelatin thickness of 0.22 mm). The "X" data points were obtained from 60 mg 2-butanol placed into a single hardgel capsule (total gelatin thickness of 0.11 mm).

The plot in FIG. 4 shows detection (sensitivity) of 2-butanone, the major ketone metabolite of 2-butanol, in the breath of individuals ingesting the capsules at various times post capsule ingestion. Based on receiver operating characteristic (ROC) curve analyses and using a validated miniature gas chromatogram-based gas sensor with an automated breath capture system to quantitate 2-butanone breath levels, a rise in 2-butanone breath concentrations ≥5 ppb above baseline values was determined to be the cutoff value.

For the capsules described herein, the "thick softgel" capsules have a wall thickness of 0.76 mm, the "thin softgel" capsules have a wall thickness of 0.51 mm and the hardgel capsules have a thickness of 0.11 mm. The diamond (♦) and triangle (▲) data points are from separate studies wherein the subjects ingested 40 mg of 2-butanol contained within thick softgel capsules (composition: 40 mg 2-butanol, 18.6 mg PEG-400, 10 mg vanillin, and 1.4 mg DL-menthol) placed in a hardgel capsule (total gelatin thickness of 0.87 mm). In the diamond (♦) study, 113 subjects were tested over 339 subject-visits and in the triangle (▲) study, 44 subjects were tested over 44 subject-visits. For the inverted triangle (▼) data points, the subjects ingested 50 mg of 2-butanol (with 20 mg PEG-400) placed inside thin softgel capsules that were placed inside hardgel capsules (total gelatin thickness of 0.62 mm). 115 subjects were tested over 341 subject-visits. The square (■) data points represent a study with 31 subjects over 91 subject-visits ingesting 40 mg 2-butanol (with 18.6 mg PEG-400, 10 mg vanillin and 1.4 mg DL-menthol) in hard gel capsules placed in another hard gel capsule (total gel thickness of 0.22 mm). The black circle (●) and white circle (○) represent experiments with 50 subjects over 50 subject-visits each, whereby the subjects ingested 40 mg of 2-butanol placed in a hardgel capsule placed inside another hardgel capsule (total gelatin thickness of 0.22 mm). In the black circle (●) study, neat (no excipients added) 2-butanol was placed in the first hardgel capsule, while in the white circle (○) experiment, 40 mg 2-butanol was placed in the first hardgel capsule with 18.6 mg PEG-400, 10 mg vanillin and 1.4 mg DL-menthol. Finally, in the "X" experiment (N=51), subjects ingested 60 mg 2-butanol, 60 mg 2-pentanone and 30 mg L-carvone inside into a single hardgel capsule (total gelatin thickness of 0.11 mm).

Thus, it can be seen that the ingestion of the 2-butanol MAM was detected at earlier times as the thickness of the gelatin layer was decreased. For medication adherence monitoring devices that detect compounds in the breath (and for some other MAMs as well), a relatively thin wall between the MAM and the outside environment may be desirable in order to more quickly detect the detectable markers (see FIG. 5 below) relatively soon after ingestion. This may improve compliance with medication adherence monitoring regimens.

Figure 5:
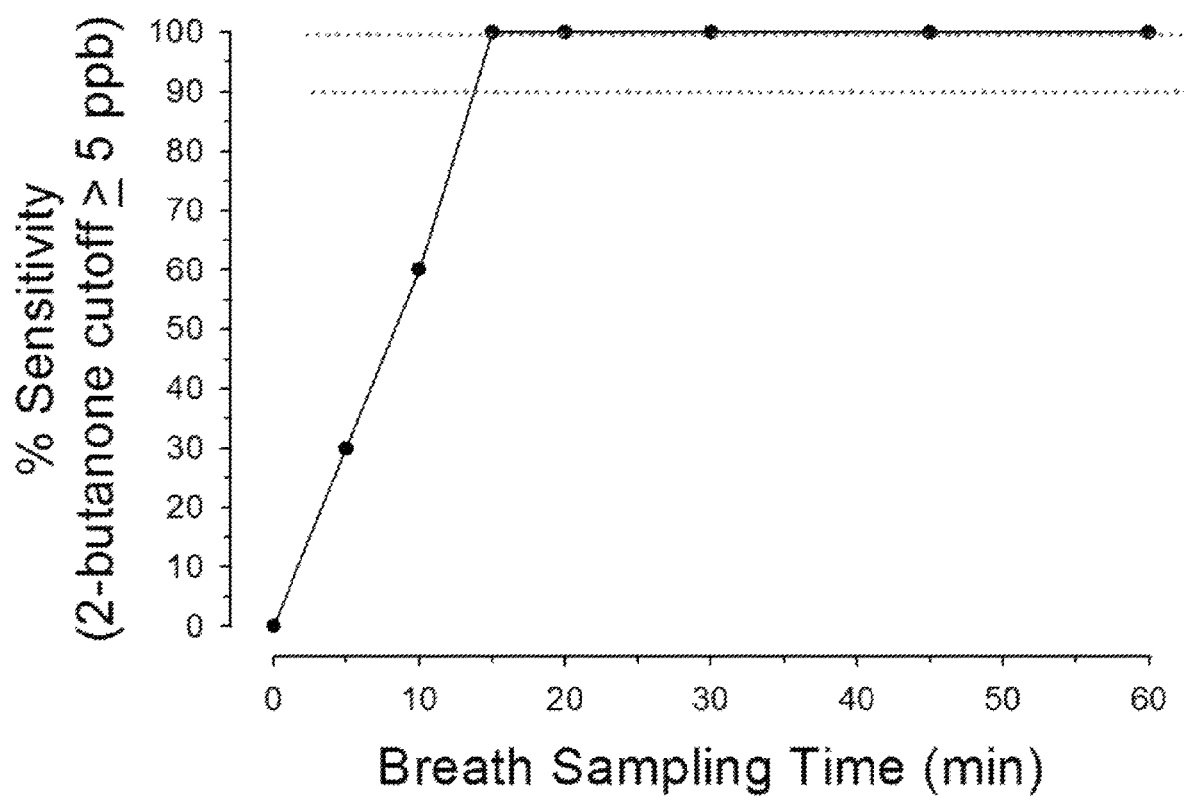
FIG. 5 shows a graph plotting the detection (sensitivity) of 2-butanol ingestion (as measured by a rise in 2-butanone breath levels ≥5 parts per billion [ppb] above baseline values) in humans over time using AdhCap illustrated in FIG. 2B.

In terms of rapidity of detecting the ingestion of capsules containing the MAM, 2-butanol, FIG. 5 illustrates how the DB adherence capsule design (illustrated in FIG. 2B: total gel wall thickness 0.11 mm; adherence sheath sealed to capsule head with LEMS) can improve performance. Specifically, among capsule designs where the MAM is physically separated from the space containing the API, the adherence capsule (FIG. 2B) markedly shortens the time required to detect 2-butanone in the breath, compared to other capsule designs shown in FIG. 4. Specifically, the performance of the DB adherence capsule (design: FIG. 2B) closely mimics that of placing 2-butanol directly into a hard gel capsule (indicated by the symbol X in FIG. 4). The DB adherence capsule design provided sensitivity values of 60% and 100% at 10 and 15 min, respectively. In this example, the payload space in the DB adherence capsule contained 50 mg 2-butanol (125 mg of 40%$_{w/w}$ 2-butanol maltodextrin powder). Data shown is from 10 subjects fed ad lib and having a wide demographic profile with no enrollment exclusions.

In the drawings and specification, there have been disclosed embodiments of the invention and, although specific terms are employed, they are used in a generic and descriptive sense only and not for purposes of limitation, the scope of the invention being set forth in the following claims.

I claim:

1. A pharmaceutical capsule for medication adherence monitoring, comprising:
   a capsule body and a capsule cap, wherein the capsule cap envelops an open end of the capsule body to form a capsule core; and
   an additional capsule cap or an additional capsule body that envelops and is sealed to a portion of the capsule core such that a payload space is formed between the additional capsule cap or the additional capsule body and the capsule core, wherein the additional capsule cap, if present, is the same as or a modified version of the capsule cap, and wherein the additional capsule body, if present, is the same as or a modified version of the capsule body.

2. The pharmaceutical capsule of claim 1, wherein the additional capsule cap or the additional cap or the additional capsule body is sealed to the capsule core with a circumferential band.

3. The pharmaceutical capsule of claim 1, wherein the additional capsule cap or the additional capsule body is chemically sealed to the capsule core.

4. The pharmaceutical capsule of claim 1, wherein the additional capsule cap or the additional capsule body envelops and is sealed to a capsule body portion of the capsule core.

5. The pharmaceutical capsule of claim 1, wherein the additional capsule cap or the additional capsule body envelops and is sealed to a capsule cap portion of the capsule core.

6. The pharmaceutical capsule of claim 1, further comprising a medication adherence marker (MAM) contained in the payload space formed between the additional capsule cap or the additional capsule body and the capsule core.

7. The pharmaceutical capsule of claim 6, wherein the MAM is present in the payload space between the additional capsule cap or the additional capsule body and the capsule body portion of the capsule core.

8. The pharmaceutical capsule of claim 6, wherein the MAM is present in the payload space between the additional capsule cap or additional capsule body and the capsule cap portion of the capsule core.

9. The pharmaceutical capsule of claim 6, wherein the MAM is a solid at standard temperature and pressure.

10. The pharmaceutical capsule of claim 6, wherein the MAM is a liquid at standard temperature and pressure.

11. The pharmaceutical capsule of claim 6, wherein the MAM comprises a secondary or tertiary alcohol.

12. The pharmaceutical capsule of claim 6, wherein the MAM comprises an electronic device.

13. The pharmaceutical capsule of claim 1, wherein the the additional capsule cap or the additional capsule body has a thickness in a range of 0.08 to 0.13 mm.

14. The pharmaceutical capsule of claim 1, wherein the additional capsule cap or the additional capsule body has a thickness of 0.11 mm.

15. The pharmaceutical capsule of claim 1, wherein the capsule cap, capsule body, and additional capsule cap or the additional capsule body comprise a hard-shell gelatin material.

16. The pharmaceutical capsule of claim 1, wherein the capsule cap, capsule body, and the additional capsule cap or the additional capsule body comprises a vegan or vegetarian material.

17. A method of forming a pharmaceutical capsule for medication adherence monitoring, comprising enveloping an open end of a capsule body with a capsule cap to form a capsule core; and enveloping a portion of the capsule core with an additional capsule cap or an additional capsule body, such that a payload space is formed between the additional capsule cap or the additional capsule body and the capsule core; and sealing the additional capsule cap or the additional capsule body to the capsule core, wherein the additional capsule cap, if present, is the same as or a modified version of the capsule cap, and wherein the additional capsule body, if present, is the same as or a modified version of the capsule body.

18. The method of claim 17, wherein the seal is formed by securing a band circumferentially around a portion of the additional capsule cap or the additional capsule body that envelops the portion of the capsule core.

19. The method of claim 17, wherein the seal is formed by chemically bonding a portion of the additional capsule cap or the additional capsule body to the capsule core.

20. The method of claim 17, wherein the additional capsule cap or the additional capsule body envelops a capsule body portion of the capsule core.

21. The method of claim 17, wherein the additional capsule cap or the additional capsule body envelops a capsule cap portion of the capsule core.

22. The method of claim 17, further comprising placing a medication adherence marker (MAM) in the additional capsule cap or the additional capsule body before enveloping the portion of the capsule core with the additional capsule cap or the additional capsule body.

23. The method of claim 22, wherein the MAM is a solid at standard temperature and pressure.

24. The method of claim 22, wherein the MAM is a liquid at standard temperature and pressure.

25. The method of claim 22, wherein the MAM comprises a secondary or tertiary alcohol.

26. The method of claim 22, wherein the MAM comprises an electronic device.

27. The method of claim 17, wherein the additional capsule cap or the additional capsule body has a thickness in a range of 0.08 to 0.13 mm.

28. The method of claim 27, wherein the additional capsule cap or the additional capsule body has a thickness of 0.11 mm.

29. The method of claim 17, wherein the capsule cap, capsule body, and the additional capsule cap or the additional capsule body comprise a hard-shell gelatin material.

30. The method of claim 17, wherein the capsule cap, capsule body, and the additional capsule cap or the additional capsule body comprise a vegan or vegetarian material.

* * * * *

UNITED STATES PATENT AND TRADEMARK OFFICE
CERTIFICATE OF CORRECTION

PATENT NO. : 10,772,831 B2  
APPLICATION NO. : 15/627699  
DATED : September 15, 2020  
INVENTOR(S) : Donn Dennis Page 1 of 1

It is certified that error appears in the above-identified patent and that said Letters Patent is hereby corrected as shown below:

In the Claims

Column 9, Line 24, Claim 7: Please correct "cap or or the" to read -- cap or the --

Column 9, Line 45, Claim 15: Please correct "and additional" to read -- and the additional --

Column 9, Lines 38-39, Claim 13: Please correct "wherein the the additional" to read -- wherein the additional --

Column 9, Line 50, Claim 16: Please correct "comprises" to read -- comprise --

Signed and Sealed this  
Twenty-seventh Day of July, 2021

Drew Hirshfeld  
*Performing the Functions and Duties of the*  
*Under Secretary of Commerce for Intellectual Property and*  
*Director of the United States Patent and Trademark Office*